US009603921B2

(12) United States Patent
Moser et al.

(10) Patent No.: US 9,603,921 B2
(45) Date of Patent: Mar. 28, 2017

(54) VIROSOME PARTICLES COMPRISING ANTIGENS FROM INFLUENZA VIRUS AND HEPATITIS B VIRUS

(75) Inventors: Christian Moser, Kehrsatz (CH); Giovanna Assero, Catania (IT); Epifanio Fichera, Enna (IT); Dario Ventura, Catania (IT); Laurence Lempereur, Catania (IT); Diana Felnerova, Bern (CH)

(73) Assignee: Janssen Vaccines AG, Leiden (NL)

( * ) Notice: Subject to any disclaimer, the term of this patent is extended or adjusted under 35 U.S.C. 154(b) by 2100 days.

(21) Appl. No.: 11/666,633

(22) PCT Filed: Oct. 20, 2005

(86) PCT No.: PCT/EP2005/011297
§ 371 (c)(1),
(2), (4) Date: Oct. 28, 2008

(87) PCT Pub. No.: WO2006/045532
PCT Pub. Date: May 4, 2006

(65) Prior Publication Data
US 2009/0087453 A1 Apr. 2, 2009

(30) Foreign Application Priority Data

Oct. 27, 2004 (EP) ..................... 04025573

(51) Int. Cl.
A61K 39/145 (2006.01)
A61K 39/29 (2006.01)
A61K 39/12 (2006.01)
A61K 39/00 (2006.01)

(52) U.S. Cl.
CPC .......... A61K 39/292 (2013.01); A61K 39/12 (2013.01); A61K 39/145 (2013.01); A61K 39/29 (2013.01); A61K 2039/5252 (2013.01); A61K 2039/5258 (2013.01); A61K 2039/55572 (2013.01); C12N 2730/10134 (2013.01); C12N 2760/16134 (2013.01)

(58) Field of Classification Search
None
See application file for complete search history.

(56) References Cited

U.S. PATENT DOCUMENTS

| 4,624,918 | A | * | 11/1986 | Hershberg | .................... 435/70.1 |
| 5,879,685 | A | | 3/1999 | Glueck et al. | |
| 6,020,167 | A | | 2/2000 | Thoma | |
| 2003/0180351 | A1 | | 9/2003 | Gluck | |
| 2004/0156863 | A1 | * | 8/2004 | Page et al. | ................. 424/189.1 |
| 2004/0202676 | A1 | | 10/2004 | Rubido | |

FOREIGN PATENT DOCUMENTS

| EP | 1 346 727 A | 9/2003 |
| WO | WO 92/19267 | 11/1992 |
| WO | WO 92/19268 | 11/1992 |
| WO | WO 95/32706 | 12/1995 |
| WO | WO 98/52603 | 11/1998 |
| WO | WO 99/39736 | 8/1999 |
| WO | WO 00/32625 | 6/2000 |
| WO | WO 2004/045582 A | 6/2004 |

OTHER PUBLICATIONS

Bagai et al., FEBS Letters, 1994, 353:332-336.*
Evans et al., Expert Rev. Vaccines, 2003, 2(2):219-229.*
PCT International Search Report, PCT/EP2005/011297, dated May 30, 2006.
PCT International Preliminary Report on Patentability, PCT/EP2005/011297, dated Jan. 19, 2007.
Bruss, Evelopment of the hepatitis B. virus necleocapsid, Virus Research, Sep. 29, 2004, pp. 199-209, vol. 106, No. 2.
Huckriede et al. Influeza Virosomes in Vaccine Development, Methods in Enzymology, 2003, pp. 74-91, vol. 373.
Gluck et al., Influenza virosomes as an efficient system for adjuvanted vaccine delivery, vaccines and Antibodies, Expert Opinion on Biological Therapy, Jul. 2004, pp. 1139-1145, vol. 4, No. 7.
Haglund et al., Expression of Human Immunodeficiency Virus Type 1 Gag Protein Precursor and Envelope Proteins from a Vesicular Stomatitis Virus Recombinant: High Level Production of Virus-like Particles Containing HIV Envelope, Virology, 2000, pp. 112-121, vol. 268.
Latham et al., Formation of Wild-Type and Chimeric Influenza Virus-Like Particles following Simultaneous Expression of Only Four Structural Proteins, Journal of Virology, Jul. 2001, pp. 6154-6165, vol. 72, No. 13.
Bungener et al., Virosome-mediated delivery of protein antigens in vivo: efficient induction of class I MHC-restricted cytotoxic T lymphocyte activity, Vaccine, 2005, pp. 1232-1241, vol. 23, Elsevier.
Hunziker et al., In vitro studies of core peptide-bearing immunopotentiating reconstituted influenza virosomes as a non-live prototype vaccine against hepatitis C virus, International Immunology, 2002, pp. 615-626, vol. 14, No. 6.
Kumar et al., A 45,000-$M_2$ Glycoprotein in the Sendai Virus Envelope Triggers Virus-Cell Fusion, Journal of Virology, Sep. 1997, pp. 6398-6406, vol. 71, No. 9.
Morein et al., Subunit vaccines against enveloped viruses: virosomes, micelles and other protein complexes, Vaccine, Jun. 1985, pp. 83-93, vol. 3.

* cited by examiner

Primary Examiner — Stacy B Chen
(74) Attorney, Agent, or Firm — TraskBritt, P.C.

(57) ABSTRACT

The present invention provides a virosome comprising a virosomal membrane comprising at least one lipid and envelope proteins of an enveloped virus and of the virosome and attached to said envelope proteins. Furthermore, the invention provides a vaccine comprising the virosome of the invention and, a method for the production of a virosome of the invention. Moreover, the invention provides a use of a virosome of the invention for the preparation of a vaccine, e.g. for the prevention or alleviation of a disease related to an HBV infection, and a method for the vaccination of a subject.

18 Claims, 10 Drawing Sheets

Figure 3

Figure 1:
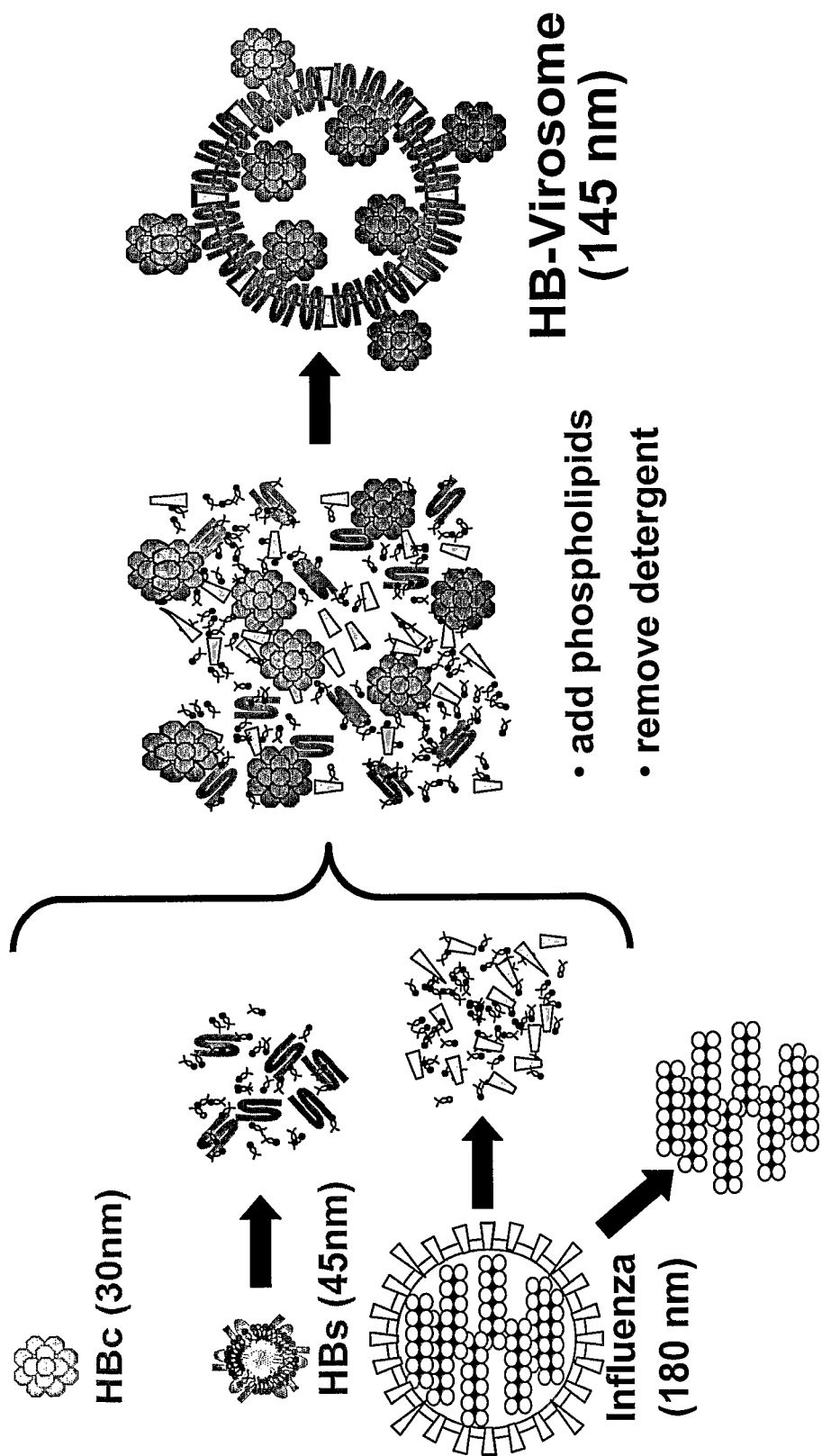

Experimental design:
Antigen mix HA+HBs+HBc (lanes 1-4) and HB-Virosomes containing the same amount of antigen were either incubated in the absence (lanes 1 and 5) or in the presence of trypsin (lanes 2/6: 2h, lanes 3/7: 5h, lanes 4/8: 10h). After incubation, the samples were analysed by SDS-PAGE and Western blot against HBc and HBs.

Figure 10

| PARAMETER | ANTI-HBS | ANTI-HBC |
|---|---|---|
| serology | | |
| IgG | +++ | +++ |
| with adjuvant (RC529) | IgG2↑ | IgG2↑ |
| | | |
| splenocytes/FACS | | |
| CD8/IFN-g | ++ | +/- |
| CD8/Pentamer | nd | + |
| CD4/IFN-g | nd | + |
| | | |
| splenocytes/ELISPOT | | |
| MHCI-pep/IFN-g | +++ | + |
| protein/IFN-g | +++ | + |

VIROSOME PARTICLES COMPRISING ANTIGENS FROM INFLUENZA VIRUS AND HEPATITIS B VIRUS

CROSS-REFERENCE TO RELATED APPLICATION(S)

This application is a national stage filing under 35 U.S.C. §371 of PCT/EP05/11297, filed Oct. 20, 2005, and published on May 4, 2006 in English as WO 2006/045532 A2, which itself claims priority from EP 04025573.9, filed Oct. 27, 2004.

The present invention relates to a virosome comprising a virosomal membrane comprising at least one lipid and envelope proteins of an enveloped virus and nucleocapsid particles of said enveloped virus located on the inside and the outside of the virosome and attached to said envelope proteins. Furthermore, the invention relates to a vaccine comprising the virosome of the invention and a method for the production of a virosome of the invention. Moreover, the invention relates to a use of a virosome of the invention for the preparation of a vaccine, e.g. for the prevention or alleviation of a disease related to an HBV infection, and a method for the vaccination of a subject.

Several documents are cited throughout the text of this specification. The disclosure content of each of the documents cited herein (including any manufacturer's specifications, instructions, etc.) is herewith incorporated by reference.

The development of novel and increasingly safer vaccines frequently makes use of well-characterized antigens, in particular highly purified recombinant proteins or synthetic peptides. In spite of some achievements, this approach is impeded by the fact that such antigens are often poor immunogens when administered alone. This fact has necessitated the development of suitable adjuvant and carrier systems that possess the ability to enhance the immunogenicity of a given antigen. One possible approach is the integration of antigens into a higher structure, e.g. a virus-like particle. The physical association of all vaccine components in a single particle ensures their simultaneous interaction with individual immune cells, and thereby, maximal exploitation of synergistic potentials. This is of particular relevance if immuno-stimulatory or immuno-modulatory components (adjuvants) are included in the formulation. Furthermore, the particle structure itself can have immuno-stimulatory effects and increase both, the stability and the immunogenicity of the individual components.

It is thus a problem to find a suitable approach of combining the relevant antigens in an industrial applicable formulation, which leads to an efficient prophylactic and/or therapeutic application.

During a virus replication in a host cell, copies of the viral genome are generated and viral proteins are expressed and processed before they assemble to mature virions while taking advantage of the cellular infrastructure. The common basis is that virus replication and assembly of progeny requires the environment of a living host cell and an ordered series of specific interactions between viral nucleic acids, viral and host cell proteins, and lipid membranes, that leads to segregation and assembly of the macromolecular virion structure. The large number of different molecules required and in addition, the cellular structures involved illustrate the high complexity of any virion assembly. There are major differences between different virus classes, and in particular, between enveloped and non-enveloped viruses. Common to all enveloped viruses is the outer shell of the virus, composed of a lipid membrane with integrated viral proteins, and, as a consequence, the necessary interaction between membrane-associated and soluble viral proteins or protein-based structures, e.g. the nucleocapsids in order to assemble a mature enveloped virus. Non-enveloped viruses lack a lipid-based membrane and assemble from protein and nucleic acid molecules only.

Numerous approaches to reconstitute viral particles in vitro and in vivo have been described in the literature and can be divided into distinct categories:

(a) In Vitro Reconstitution of Viral Envelopes

Virus-derived or recombinant envelope proteins can be purified and formulated with or without additional lipids into proteoliposomes. This pure in vitro approach achieves the generation of the outer shell of enveloped viruses, the envelope, but does not include the core of the virus, the nucleocapsid. There are examples of chimerical virosomal structures, which integrate envelope proteins from different viruses. Reconstituted viral envelopes have also been used successfully for gene transfer (DNA or RNA) but these methods did not depend on packaging of a functional, protein-based nucleocapsid but rather an association of the nucleic acids directly with the reconstituted envelope.

(b) Heterologous Expression of One or More Viral Proteins

Isolated recombinant viral proteins can self-assemble into virus-like structures (VLPs): HPV (yeast, baculo), HCV (baculo), HBs antigen (yeast, CHO), HBc (*E. coli*). Common to all these approaches is that the self-assembly takes place in the heterologous cellular expression system and the virus-like particles are subsequently purified. Therefore, the assembly does not take place in vitro but relies on a cellular system. VLPs have been used as vaccines and as vaccine carriers. (Pumpens, P.; Grens, E. (2001) Intervirology 44 (2-3); 98-114; Noad R, Roy P. (2003) Trends Microbiol. 111(9): 438-44)

(c) Reconstitution of Non-Enveloped (Icosahedral) Viruses or Virus-like Particles in Vitro This approach is based on separately purified components. Due to the absence of a lipid membrane-based envelope, non-enveloped viruses are simpler in their structure and can self-assemble under certain conditions in vitro if all necessary components are present in the correct stoechiometry. Similarly, the inner core of enveloped viruses, the lipid-free nucleocapsids, or subunits thereof have been reconstituted in vitro from purified recombinant components, e.g. of influenza virus (Martin-Benito J. et al. (2001) EMBO Rep. 2(4): 313-7).

(d) Purification of Viral Nucleocapsids

Nucleocapsids have been extracted and purified from many different virus types in order to characterise their composition. These preparations can also be used for transfection of susceptible cells aiming at virus rescue. Successful virus rescue implies that a functional nucleocapsid was isolated and delivered to the cytoplasm of a host cell. However, this does not imply the successful reconstitution of a functional enveloped virus, because the natural way of infection, which depends on a functional envelope, is bypassed by the use of a transfectant, the latter mediating direct delivery of the nucleocapsid into the cytoplasm of a host cell.

(e) Pseudotyping of Enveloped Viruses and Viral Vectors in a Cell Culture System.

This in vivo approach has been widely and successfully used for the production of chimerical viruses or vectors (e.g. Retroviruses, Lentiviruses, and AAV) at lab scale. The key element for the production of pseudotyped viruses is a helper cell that co-expresses all the proteins to be integrated into the virion and mediates assembly of the virions. In contrast, an in vitro assembly of an enveloped virus is based on defined, separately produced and purified components, and the physical association is performed under controlled conditions in vitro. (Sandrin V. et al. (2003) Curr Top Microbiol Immunol.; 281:137-78)

As a specific form of virus-like particles, virosomes are a clinically proven vaccine carrier/adjuvant system with an excellent safety and tolerability profile in humans. The capability of the virosomal carrier to mediate antigen processing through both the exogenous and the endogenous pathway makes this system a good candidate for a therapeutic vaccine.

The basic concept of virosomes comprises the reconstitution in vitro of empty viral envelopes, or more general, of viral envelope proteins integrated into a spherical lipid bilayer. Virosomes have been generated from a number of viruses (Y Kaneda. (2000) Adv. Drug Delivery Rev. 43, 197-205; Drummond D C. et al. (2000) Prog Lipid Res. 39(5): 409-60). The possibility of producing chimerical virosomes containing envelope proteins from two different viruses has been demonstrated (Bagal S. Sarkar D P. (1994) FEBS Lett. 353(3): 332-6).

In all cases, the viral protein of interest is a transmembrane or membrane-anchored structure, which is prerequisite for spontaneous integration.

The virosomal formulation of molecules that do not directly interact with the virosomal lipid membrane is far more difficult to achieve. Although the idea of linking molecules to virosomal structures has been proposed earlier (WO 95/32706, INEX), the technical hurdles to achieve stable and efficient formulations can be enormous, depending on the biochemical properties of the molecule of interest. Nucleic acids can be associated to the virosomal structure via the use of positively charged lipids (WO 98/52603, Berna). Small molecules (peptides, drugs) lacking a secondary and tertiary structure for their function can be modified biochemically in order to enable association, integration or encapsulation. A number of methods have been described for virosomal formulation, in particular, encapsulation of small molecules (Wälti et al, (2002) Canc. Res) or synthetic particles (Jana et al. (2002) FEBS Lett.; 515(1-3: 184-188). These methods only work under chemical conditions that would affect the authentic conformation of larger proteins and even more so, the integrity of multimeric protein complexes such as viral nucleocapsids (e.g. the HBc antigen particle). The methods described so far to associate one or more large proteins lacking exposed lipophilic domains into the virosomal membrane required biochemical modifications of the protein, e.g. covalent linkage to lipid molecules (Hunziker I P. et al. (2002) Int Immunol. 14(6): 615-26), in order to anchor the respective protein in the lipid membrane. This method has also proven efficacious for retargeting virosomes to specific cell types via crosslinked antibodies (Mastrobattista E. et al. (2001) FEBS Lett. 509(1): 71-6., Wälti et al, Canc. Res. 2002). However, biochemical modifications require conditions (e.g. oxidative conditions for activation of reactive side groups) which are likely to dissociate non-covalently linked multimeric structures (e.g. a viral nucleocapsid). In addition, such conditions can also alter the conformation of the protein molecule in question, and, as a consequence, impact on its immunogenicity, and ultimately, on the efficacy of the vaccine. Furthermore, the crosslinking procedure increases both the number of steps required for the formulation and the loss of antigen. Only one example exists for a multimeric protein structure successfully associated with virosomes without biochemical modification, namely the Hepatitis A vaccine Epaxal® (Glück R., 1995, J. of Liposome Research 1995, 5(3), 467-479). However, in this vaccine the antigen is associated to the outer surface only after formulation of influenza virosomes, due to electrostatic interaction between virosomal membrane and virus particle. As a consequence, no antigen is located in the aqueous interior of the virosome, which is the preferred location for efficient cytoplasmatic delivery and induction of a CD8-based cellular response as it will be required for a therapeutic vaccine. (Bungener L. et al. (2002) J Liposome Res. 12(1-2): 155-63; Bungener L. et al. (2002) Vaccine. 20(17-18): 2287-95.)

The potential and the limitation of approaches for the prevention and the treatment of infectious diseases are discussed herein below exemplarily for HBV. HBV infection represents a huge health problem world-wide, in particular because of life threatening late complications. The World Health Organisation (WHO) estimates that currently approximately 400 million individuals are chronic HBV carriers. Patients suffering from chronic HBV infection show a wide range of symptoms, from clinically inapperent to severe chronic liver disease, yet the long-term risk of liver disease (chronic hepatitis, cirrhosis and hepatocarcinoma) is dramatically increased for all chronic HBV carriers (25% incidence within 20 to 30 years after infection). Common to all chronic patients is also a poor immune response to the causative agent, HBV, and, in particular, against the HBV core protein (HBc), despite of the fact that large amounts of antigen are circulating throughout the chronic infection. In contrast, resolution of acute Hepatitis B, as well as the spontaneous or treatment-induced resolutions of chronic Hepatitis B, is strictly associated to the development of a broad and vigorous immune response against HBV antigens. Conventional therapeutic approaches, such as therapies with interferon or antiviral drugs to control chronic hepatitis are only partially successful, yet cost-intensive and associated with significant side-effects. Patients with HBV-associated chronic hepatitis would thus greatly benefit from a therapeutic vaccine that can control this persistent virus infection.

According to the current understanding of HBV pathogenesis and immunology, the key to a successful therapeutic vaccination is to overcome the HBV-specific immunological non-responsiveness of chronic carriers. To that end, the relevant antigens (HBc and HBs) must be presented to the patient's immune system in a way that the existing inefficient Th2 type (humoral) immunity is skewed into a strong and sustained Th1 type (cellular) of response, and at the same time, boost the Th2 type response.

The immune response against the relevant antigens should be broad and directed simultaneously against many different epitopes in order to prevent immune-escape mutants of the virus. Such variants have been shown to evolve under selective pressure directed against single epitopes. Furthermore, the use of full-length proteins as antigens of the vaccine takes in account the genetic diversity of the patients with regard to antigen processing and MHC genotype-dependent, epitope selection.

Significant efforts have been dedicated to the development of therapeutic HBV vaccines in the past, as reviewed by M. Hilleman (Vaccine 21 (2003): 4626-4649). In a number of clinical trials, conventional HBs-based prophylactic vaccines have been used in chronic HBV patients, but no sustained positive effects were observed so far. Peptidebased vaccines intended to focus the immune response to fen relevant epitopes (reviewed by Engler et al., Mol. Immunol. 2001 Dec. 38(6): 457-65). This approach yielded promising results in preclinical research but not in humans. More recently, recombinant HBc particles were produced which carried single epitopes of HBs on the surface in an attempt to combine the two relevant HBV antigens in one vaccine (Chen et al, Vaccine. 2004 Jan. 2; 22(3-4): 439-46).

These approaches mainly aim at humoral response of the immune system. The more advanced approaches follow the concept that a cellular response (Th1 type) against HBV is a key element of a successful therapeutic immunisation.

The induction of a Th1-type immune response against the HBV antigens, especially against HBc, is the ultimate goal of a therapeutic HBV vaccine. While HBs alone can elicit a Th1 response to some degree, HBc alone does not. Therefore, these antigens alone cannot induce the adequate immune response required for a therapeutic effect. It can only be achieved by combination of the HBV antigens with a Th1-supporting adjuvant or carrier system. In contrast, aluminium salts, the most widely used adjuvant in current human vaccines, are well known to abolish Th1 responses in favour of a Th2 response. This property of aluminium salts makes it a very attractive adjuvant for prophylactic vaccines, which are primarily aiming at the induction of high titre of protective antibodies. In a therapeutic setting, a sustained Th1 response plays a crucial role since Th1 effector cells mediate control of virus replication and elimination of virus-infected cells.

Attempts were made with DNA vaccines (plasmid DNA encoding the HBV core or S genes) known to promote primarily a cellular response. Despite the fact that DNA vaccines work very well in the mouse model, numerous clinical trials have failed to provide proof of principle in man, not only in the HBV field. Similarly, the use of viral vectors expressing HBV antigens (e.g. vaccinia) aiming at enhancing cellular response failed to induce significant and sustained responses in humans.

Although various approaches have been tested for therapeutic HBV vaccines none of those lead to a sufficient therapeutic vaccine.

The two major structural HBV proteins, HBs and HBc can be expressed individually in several heterologous systems: *E. coli*, yeast, and mammalian cell lines. Both antigens form typical virus-like particle structures (HBs particles and HBc particles, respectively) which are clearly distinct from the infectious, enveloped, and nucleocapsid-containing HBV virions.

Recombinant Hepatitis B core antigen (HBc) can be produced in a bacterial or a yeast-based expression system, since this protein is not glycosylated. HBV core monomers self-assemble into virus-like particles with a diameter of about 30 nm and can be purified in this form from the producer cells. Very similar to authentic H BV nucleo-capsids, HBc particles are composed of either 180 or 240 monomeric core molecules which self-assemble into the particle structure. HBc particles do not contain lipids. The HBV core monomer consists of 183 to 185 amino acid (aa) residues (length is isolate-dependent). The C-terminal 30 aa feature a nucleic acid binding domain, which results in the presence of, significant amounts of nucleic acids (predominantly RNA derived from the expressing cell in the absence of HBV genomes) in purified preparations of HBc particles, an unwanted contamination. HBc can be truncated at the C-terminus to a length of 144 aa, which reduces the nucleic acid content by 99% while retaining the particle structure. Shorter constructs than 144 aa do not form particles any more.

The production of recombinant HBc particles has been described in many variants. Engineered variants of HBc have been used as a carrier system for heterologous antigens (Pumpens, P.; Grens, E. (2001) Intervirology 44 (2-3); 98-114). In this approach the foreign aa sequence is inserted in the region (aa 70-90) of the protein chain which is exposed to the outer surface in the context of the multimeric particle. However, the size of the genetically inserted foreign antigen sequence is very limited due to the necessity that the monomers retain their capability to self-assemble into particles. When used as a vaccine in animal models, HBc particles alone induce a significant humoral response but lack the ability to produce a HBc-specific CD8-type cellular response which is considered essential for a therapeutic effect.

WO 00/32625 (Biogen) describes Hepatitis B core particles comprising immunogens, epitopes resulting potentially in multivalent hepatitis B core particles.

An approach already entering clinical trials is the construction of a modified Hepatitis B core particle containing multiple epitopes of *Plasmodium falciparum* for prevention of Malaria (Birkett A., et al, Infection and Immunity 2002, p 686-6870)

The authentic HBV envelope protein (HBs) exists in three forms L (large), M (middle), S (small) which are expressed from three staggered translation start sites. All three forms of HBs in multimeric form are present in the envelope of HBV virions. The C-terminal preS1 (L) and preS2 (M) domains are involved in the binding of HBV to cells during infection, and antibodies against the preS1 domain are capable of neutralising HBV. When expressed as recombinant protein in yeast or mammalian cells, HBs is secreted in the form of micelle particle structures with a diameter 35-45 nm, which contain also significant amounts (60% w/w) cellular membrane lipids (Satoh O. et al. (2000) J Biochem; 127(4): 543-50). Depending on the expression construct, the recombinant particles contain either S alone or include the C-terminal pre S1 and/or pre S2 domains.

All current prophylactic vaccines against HBV are based on recombinant HBV envelope (HBs) proteins formulated with Aluminium salts. Most products are based on yeast expression. More recent products, so-called 3rd generation HBV vaccines are derived from mammalian cells. These vaccines contain the preS domains and, in addition, the authentic mammalian glycosylation pattern and a mammalian lipid composition, both of which are thought to be beneficial for a immune response.

The use of HBs particles as a vaccine carrier is claimed in WO 99/39736 (Yissum) but the system is limited to monomeric antigens thereby excluding a co-formulation with HBc particles or other nucleocapsid-type structures. In addition, the said system does not foresee a destruction and re-assembly procedure in vitro of the carrier particle.

A recent publication (Ponsel and Bruss, (2003) JV 77 416-422) describes the formation and secretion of HBV particles containing both HBs and HBc from mammalian cells co-transfected with expression plasmids for both antigens. However, there are no reports on the reconstitution of in vitro enveloped particles containing both HBs and HBc antigen.

U.S. Pat. No. 6,020,167 (Medeva) claims a method of treating Hepatitis B by administering a composition comprising one or more T cell activating epitopes from pre S1 or HBV core and a carrier capable of presenting the polypeptide. The carrier according to the invention can be a HBsAg particle.

As a specific form of virus-like particles, virosomes are a clinically proven vaccine carrier/adjuvant system with an excellent safety and tolerability profile in humans.

The capability of the virosomal carrier to mediate antigen processing through both the exogenous and the endogenous pathway makes this system a good candidate for a therapeutic vaccine.

The basic concept of virosomes comprises the in vitro reconstitution of empty viral envelopes, or more general, of viral envelope proteins integrated into a spherical lipid bilayer. Virosomes have been generated from a number of viruses (Y Kaneda. (2000) Adv. Drug Delivery Rev. 43, 197-205; Drummond D C. et al. (2000) Prog Lipid Res. 39(5): 409-60). The possibility of producing chimerical virosomes containing envelope proteins from two different viruses has been demonstrated (Bagai S, Sarkar D P. (1994) FIBS Lett. 353(3): 332-6)

In all cases, the viral protein of interest is a transmembrane or membrane-anchored structure, which is prerequisite for spontaneous integration.

The virosomal formulation of molecules that do not directly interact with the virosomal lipid membrane is far more difficult to achieve. Although the idea of linking molecules to virosomal structures has been proposed earlier (WO 95/32706, INEX), the technical hurdles to achieve stable and efficient formulations can be enormous, depending on the biochemical properties of the molecule of interest. Nucleic acids can be associated to the virosomal structure via the use of positively charged lipids (WO 98/52603, Berna). Small molecules (peptides, drugs) lacking a secondary and tertiary structure for their function can be modified biochemically in order to enable association, integration or encapsulation. A number of methods have been described for virosomal formulation, in particular, encapsulation of small molecules (Wälti et al, (2002) Canc. Res) or synthetic particles (Jana et al. (2002) FEBS Lett.; 515(1-3: 184-188). These methods only work under chemical conditions that would affect the authentic conformation of larger proteins and even more so, the integrity of multimeric protein complexes such as viral nucleocapsids (e.g. the HBc antigen particle). The methods described so far to associate one or more large proteins lacking exposed lipophilic domains into the virosomal membrane required biochemical modifications of the protein, e.g. covalent linkage to lipid molecules (Hunziker I P. et al. (2002) Int Immunol. 14(6): 615-26), in order to anchor the respective protein in the lipid membrane. This method has also proven efficacious for retargeting virosomes to specific cell types via crosslinked antibodies (Mastrobattista E. et al. (2001) FEBS Lett. 509(1): 71-6., Wälti et al, Canc. Res. 2002). However, biochemical modifications require conditions (e.g. oxidative conditions for activation of reactive side groups) which are likely to dissociate non-covalently linked multimeric structures (e.g. a viral nucleocapsid). In addition, such conditions can also alter the conformation of the protein molecule in question, and, as a consequence, impact on its immunogenicity, and ultimately, on the efficacy of the vaccine. Furthermore, the crosslinking procedure increases both the number of steps required for the formulation and the loss of antigen. Only one example exists for a multimeric protein structure successfully associated with virosomes without biochemical modification, namely the Hepatitis A vaccine Epaxal® (Glück R, 1995, J. of Liposome Research 1995, 5(3), 467-479). However, in this vaccine the antigen is associated to the outer surface only after formulation of influenza virosomes, due to electrostatic interaction between virosomal membrane and virus particle. As a consequence, no antigen is located in the aqueous interior of the virosome, which is the preferred location for efficient cytoplasmatic delivery and induction of a CD8-based cellular response as it will be required for a therapeutic vaccine. (Bungener L. et al. (2002) J Liposome Res. 12(1-2): 155-63; Bungener L. et al. (2002) Vaccine. 20(17-18): 2287-95.)

A number of patents have been applied/granted for influenza virosomes (WO92/19267 WO 98/52603, Berna) and virosome-like structures derived from other enveloped viruses (e.g. Sendai Virus). These methods comprise the solubilisation of the viral envelope, removal of the nucleocapsid containing the viral genome, followed by reconstitution of an "empty" viral envelope. Furthermore, additional antigens are either adhered to ready-made virosomes (Epaxal®) or crosslinked to lipid molecules in order to anchor them in the virosomal membrane.

In view of the above described limitations of vaccination against virus infections, the technical problem underlying the present invention was to provide improved means and methods for the vaccination of subjects for the prevention, alleviation or treatment of virus infections.

The solution to said technical problem is achieved by providing the embodiments characterized in the claims.

Accordingly, the present invention provides a virosome comprising
(a) a virosomal membrane comprising at least one lipid and envelope proteins of an enveloped virus; and
(b) nucleocapsid particles of said enveloped virus located on the inside and the outside of the virosome and attached to said envelope proteins.

The term "virosome" defines a specific form of virus-like particles (VLPs). Virosomes are semi-synthetic complexes derived from viral particles and produced by an in vitro procedure. They are essentially reconstituted viral coats, while the viral nucleocapsid is replaced by a compound of choice. Virosomes retain their fusogenic activity and thus deliver the incorporated compound (antigens, drugs, genes) inside the target cell. They can be used for vaccines, drug delivery, or gene transfer.

VLPs are particle structures that are in size and shape reminiscent of or even indistinguishable from their parental virus but are lacking the capability to infect and replicate in host cells. VLPs are multimeric structures composed of viral proteins (authentic or modified variants of it). In addition, VLPs may or may not contain nucleic acids, lipids, and include lipid membrane structures or not. Two typical but very distinct examples for VLPs derived from a single Virus (HBV) are HBs and HBc particles.

The term "virosomal membrane" defines in the context of the present invention a spherical membrane structure that is reconstituted in vitro and that is composed of a lipid bilayer with integrated viral envelope proteins.

The term "envelope proteins" is intended to mean in the context of the present invention a protein encoded by an enveloped virus that in its nature form interacts directly with the virus lipid membrane.

In line with the present invention a broad range of lipids can be comprised in said virosomal membrane. The group of lipids comprises neutral and charged phospholipids, steroid-derived lipids, neutral and charged synthetic lipids. In addition to the purified lipids added to the formulation, the lipids contained in the viral components are also included in the final formulation, e.g. lipids derived from Influenza Virus or any other enveloped virus included or from lipid containing VLPs included in the formulation (e.g. HBs particles). These virus-derived lipids are heterogenous and reflect the lipid composition of the producer cell of the virus or the recombinant expression cell. The preferred formulations are based on phospholipids only in order to minimise the complexity of the formulation. The phospholipids used for HB-virosomes which are described in the appended examples are usually GMP-grade and preferably identical to the material used for the registered vaccines Inflexal® and Epaxal®.

The term "enveloped virus" defines in the context of the present invention a virus that includes a host-cell derived lipid membrane in the mature virion structure. Classes of enveloped viruses are listed in table 1.

The term "nucleocapsid particles" is intended to mean in the context of the present invention a particle structure composed of viral capsid proteins. This particle structure can be a VLP (composed of one or more recombinant viral capsid proteins), or a nucleocapsid complex purified from the parental virus. Whether or not the nucleocapsid particle contains nucleic acids is not relevant for formation of the particle.

Virosomes of the invention (chimerical virus-like particles) comprise the above characterized molecules physically associated in a single particle. The envelope protein in virosomes of the invention may be integrated in the surface of the virosome in the natural orientation with the interaction side for corresponding nucleocapsid particles to the inside of the virosome, as well as in an artificial orientation with the interaction side for corresponding nucleocapsid particles to the outside of the virosome. One example of such virosome is depicted in FIG. 1. The structure of the is novel class of virosomes is distinct from the particulate structures of the individual components described above, or from the original viruses. This type of particle does not exist in nature and has neither been described nor suggested in the state of the art so far as a structure generated in vitro. Thus, the particle structure represents the first enveloped virus-like particle re-assembled completely in vitro from isolated components.

Virosomes known in the art and described herein above are produced in cell-based systems. in such cell-based, system, all components must be produced in the same cell simultaneously, which restricts the choice of the expression system dramatically and forces compromises with respect to yield and scalability. The biological expression systems and metabolic processes that are difficult to control define the composition of the resulting virus-like particles, e.g. the ratio between the components. Furthermore, virus-like particles produced in cellular system must be extracted and purified subsequently without affecting the particle structure or composition in order to obtain a useful preparation.

In contrast and as described herein below, the composition of the in vitro formulation of virosomes of the invention is controllable via the input material and the chosen biochemical parameters. The simplicity of the process ensures its robustness. The resulting formulation does not require further purification. The individual components may be produced beforehand in separate cell-based systems (e.g. *E. coli*, mammalian cells, and yeast), and for each component, the optimal system with regard to yield, scalability and purity can be chosen.

The formulation process for virosomes of the present invention takes advantage of the interaction between viral proteins which are easily integrated into a virosome-type of structure (membrane-associated proteins, envelope proteins) and proteins that do not associate with membranes by themselves. Although this interaction is essential and efficient during the assembly of most enveloped viruses in the course of their natural replication inside a host cell, the use of this property for an in vitro formulation process of a pharmaceutical product is novel. Surprisingly, the intracellular virus assembly process can indeed be mimicked in vitro, although under completely different conditions.

Preferably the virosome is a virosome, wherein said at least one lipid comprises at least one phospholipid. More preferably, said phospholipids comprise phosphatidylcholine, phosphatidylethanolamine and phosphatitylserine.

Also envisaged by the present invention are, in a further preferred embodiment, virosomes, wherein said envelope proteins are the envelope proteins of a first and a second enveloped virus and the nucleocapsid particles are the nucleocapsid particles of said second enveloped virus.

Said first enveloped virus may be selected from any enveloped virus. Particularly preferred for the present invention are influenza viruses.

In a more preferred embodiment of the invention the envelope proteins of said first enveloped virus are hemagglutinin (HA) and/or neuraminidase (NA).

The influenza components of virosomes of the invention, hemagglutinin (HA) and neuraminidase (NA), may be purified from inactivated influenza virus (e.g. strain A/Singapore) in analogy to the established and patented formulation of influenza virosomes (Epaxal® WO 92/19267, WO 92/19268, Glück R., 1995, Journal of Liposome Research 5(3), 467-479). The influenza-derived proteins/proteins of said first enveloped virus may be included for functional rather than structural/mechanical reasons, since virosomes of the invention may also be formulated in the absence of the influenza proteins/proteins of said first enveloped virus. The influenza component may be included in order to strengthen the aspect of the virosome-like carrier immunological properties of the virosomes of the invention.

Also in line with the present invention said second enveloped virus is preferably selected from a group of enveloped virus consisting of hepatitis B virus (HBV) (which is preferred), hepatitis C virus (HCV) or any other Flavivirus, and human immunodeficiency virus (HIV).

In a further preferred embodiment of the invention the nucleocapsid particle comprises HBc protein.

HBc particles may be produced in *E. coli*, either containing the full-length amino acid sequence or truncated forms. Both the full-length as well as a truncated 144 amino acid construct were successfully formulated into HB-virosomes. Alternatively, it is contemplated that shorter (non-particular) HBV core are incorporated into HB-virosomes. Corresponding techniques are known in the art and described in the appended examples.

It is also preferred, that the envelope protein of said second enveloped virus is HBs protein.

HBs particles may contain S alone or pre S and S combined. Methods for the production of said particles are known in the art. The particles may be e.g. produced in yeast or mammalian cells. The presence of the preS domain in a vaccine comprising the virosome of the invention is likely to contribute to a broader and a more efficient immune response but has no impact on the formulation process. HB-virosomes can be produced from HBs of either source. Even the combination of different HBs types from different sources or of different serotypes into a single HB-virosome has been demonstrated using the method described here.

The current invention falls in the above preferred embodiment into the class of influenza virosomes. However, the incorporation of an envelope protein (HBsAg) of a completely unrelated virus (HBV) which is in turn used to link the nucleocapsid protein (HBc) of the same virus to the virosomal structure is completely novel.

An alternative embodiment of the invention relates to a vaccine comprising the virosome of the invention.

The term "vaccine" understood in the context of the present invention to define a prophylactic composition which is administered to a subject in the prevention of a virus disease. Alternatively or additionally, the term is intended to mean a pharmaceutical composition which is administered to a subject in the alleviation or the treatment of a virus disease.

In accordance with this invention, the terms "prophylactic composition" and "pharmaceutical composition" relate to a compositions for administration to a patient, preferably a human patient. In a preferred embodiment, said compositions comprise compositions for parenteral, transdermal, intraluminal, intraarterial, intrathecal administration or by direct injection into tissue. It is in particular envisaged that said compositions are administered to a patient via infusion or injection. Administration of the suitable compositions may be effected by different ways, e.g., by intravenous, intraperitoneal, subcutaneous, intramuscular, topical or intradermal administration. The vaccines/compositions of the present invention may further comprise a pharmaceutically acceptable excipient. Excipients used according to the invention comprise carriers, additives and dilutens such as e.g. capsules, vehicles, conservants, colourants, disintegrating agents, binders, emulsifiers, solubilisers, wetting agents, solvents, buffering agents, gel-forming agents, thickeners, film-forming agents, lubricants, glidants, form-separating agents, flow-regulating agents, sorbents and additives such as antioxidants, taste- and smell-correcting agents. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These compositions can be administered to the subject at a suitable dose. The dosage regiment will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. A preferred dosage for administration might be in the range of 1 ng to 1 mg per application.

The vaccines/compositions of the invention may be administered locally or systematically. Administration will preferably be parenterally, e.g., by biolistic delivery to an internal or external target site. Preparations for parenteral administration include sterile aqueous or non-aqueous solutions, suspensions, and emulsions. Aqueous carriers include water, emulsions or suspensions, including saline and buffered media. Parenteral vehicles include sodium chloride solution, Ringer's dextrose, dextrose and sodium chloride, or lactated Ringer's, Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. It is envisaged that the vaccines/compositions of the invention might comprise, in addition to the virosome of the invention, further biologically active agents, depending on the intended use of the compositions. Such agents might be adjuvants. An adjuvant is a substance added to a vaccine formulation to enhance or modulate the immune response against the antigens included in the vaccine. A wide variety of different adjuvants are known in the art, which are composed of lipids, proteins, carbohydrates, detergents, salts or combinations thereof.

As described in the appended examples, it has been shown that the virosomal formulation indeed improve the cellular response against the antigens. This has been particularly demonstrated by the detection of a cellular response against HBc after vaccination of mice with HB-virosomes. A sustained induction of a cellular response against a viral core antigen, e.g. HBc, and in particular, a CD8/Th1 type response, is a of advantage and particularly preferred result of the vaccination of subjects with the vaccine of the invention.

Optionally, vaccines of the invention may further comprise a pharmaceutically acceptable carrier or diluent and/or an adjuvant.

Pharmaceutically acceptable carrier or diluents are described herein below. Immuno-stimulating substances, so-called adjuvants may be added to the formulation of a vaccine of the invention in order to further increase or modulate the immune response against the antigens contained in said vaccine. A large number of compounds with adjuvant properties are known in the art. The group of such compounds comprise proteins, lipids, carbohydrates, nucleic acids and combinations thereof. The compounds may be synthetic or biologically produced. The adjuvant can be added to previously formulated virosomes, or co-formulated and integrated into the virosome structure. The latter is possible if the biochemical properties of the adjuvant allow an interaction with any of the virosome components.

It is particularly preferred, that the adjuvant is RC529 (Corixa).

Preferred HB-virosomes of the invention are, as characterized herein above, a stable, homogenous virosomal co-formulation with the influenza and the HBV antigens physically associated in a single particle. The association of the antigen with the virosomal carrier is a well-documented prerequisite for the full exploration of the immuno-stimulating effects of the virosomal antigen carrier/adjuvant system (reviewed in Moser C et al. (2003) Expert Rev Vaccines, 2(2): 189-96).

HA-mediated MHC-1 presentation of and Th1 immune response against antigen

Presentation of the antigen in a repetitive, virus-like structure

Targeting of antigen-presenting cells

Protection from extracellular degradation

With respect to a therapeutic HBV vaccine, the virosome (HA)-mediated MHC-1 presentation and targeting of dendritic cells are the most relevant features of the virosomal vaccine carrier. Therefore, it is preferred that at least part of the HBc antigen should be encapsulated into the virosome in order to be delivered to the cytoplasm of antigen-presenting cells, resulting in the induction of antigen-specific CD8 T-cells (Bungener L et al. (2002) J Liposome Res. 12(1-2) 155-63). A more recent study has demonstrated that virosomes enhanced MHC class I restricted CTL through CD4 T cell activation (Schumacher et. al, Vaccine 22 (2004): 714-723). The physical integration and incorporation, respectively, of unmodified HBs and HBc antigens represented a major technical hurdle, at the level of experimental prototype formulations, and even more so at industrial cGMP scale. Said hurdle has been overcome by the present invention. The HBV and influenza antigens used in the formulation are produced and purified separately in different recombinant expression systems (mammalian cells, yeast, or E. coli), and these purified antigens form characteristic particles by themselves.

In a further embodiment, the invention provides a method of producing a virosome comprising the steps of:
(a) solubilizing envelope proteins of an enveloped virus in the presence of a lipid in a detergent solution;
(b) decreasing the concentration of the detergent in the solution;
(c) adding nucleocapside particles of said enveloped virus to the solution obtained in step (b); and
(d) removing the detergent or the lecithin so that virosomes are produced.

The term "decreasing the concentration" is understood in the context of the present invention to include the addition of a solution without the recited detergent or the addition of a solution with a reduced concentration of the recited detergent compared to the solution obtained in step (a).

The term "removing the detergent" is understood in the context of the present invention to include processes such as dialysis, diafiltration, or chromatography. The latter, chromatography, is preferred where detergent is eliminated by absorbance to a matrix (e.g. beads, resin).

The formulation procedure of the virosomes of the invention can be adapted to a method for GMP production without further ado. As described for the example of HB-virosomes, modifications with regard to the biochemical and stoechiometric conditions are necessary in order to obtain homogenous and efficacious formulations of the novel multi-component particle structure including the HBc protein (FIG. 2) and can be carried out without an undue burden on the basis of the teachings of this specification.

The concept underlying the method of the present invention is a complete in vitro assembly of virosomes by taking advantage of the specific interaction between a viral envelope protein and the corresponding nucleocapsid or a nucleocapsid-like particle, as it occurs during intracellular virus assembly in the course of virus replication. In the examples, HBs and HBc represent a typical and preferred envelope protein and a nucleocapsid complex, respectively, but it is understood, that the invention is not limited thereto but can be applied to any enveloped virus. As a general principle, the chosen biochemical conditions during the formulation in vitro have to allow the interaction between envelope protein (env) and nucleocapsid (nc) component. The biochemical key parameters in the formulation comprise the detergent concentration, the pH-value, the osmolarity and the presence of chelators, specific salts, buffer molecules.

The presence of a detergent is required in order to dissolve the starting material (the envelope membrane of Virions or VLPs) and the lipid components. The detergent types and concentration ranges are described herein below.

The pH and the osmolarity are preferably kept as close to physiological conditions (pH 7.4, 150 mEq) as technically possible in order to reduce the risk of poor interaction or unspecific interactions with other components. For other enveloped viruses a pH range from 5 to 10, and osmolarities from 10 to 400 mEq are preferred.

Salts, chelators and buffers also influence the interaction between proteins and thus, the efficiency of a env/nc formulation. In a protocol described in the appended examples, phosphate-buffered saline solution (PBS) is used which mimics a the physiological salt composition, and comprises NaCl and the physiological buffer system Phosphate. However, for the formulation of other enveloped viruses the use of modified buffer systems (eg. Tris-based buffers or Carbonate-based buffers) in combination with NaCl, MgCl, KCl, and CaCl salts may be required. In a preferred embodiment of the invention the inclusion of chelators (eg. EDTA, EGTA) may be envisaged in order to inactivate unwanted enzymatic activities.

Figure 4:
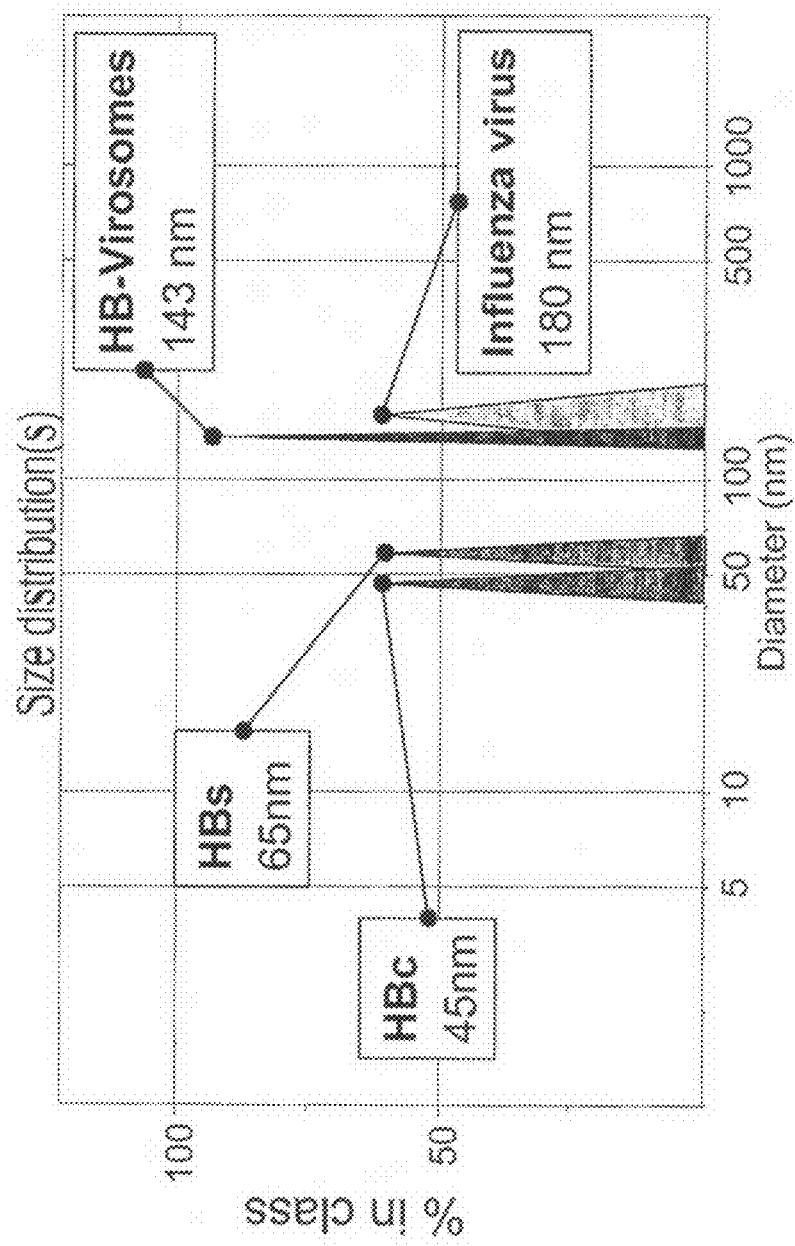

A successful formulation is best described as single, homogenous population of virus-like particles which are distinct in size, content, or biochemical properties from each of the individual starting materials (purified virus or VLPs). Differences in size are easily detected by photon correlation spectroscopy (PCS) analysis, as illustrated in FIG. 4 for HB-Virosomes in FIG. 4. The analytical method is described in example 4 (p. 33).

Whether the nucleocapsid is composed of a single recombinant protein subunit (as it is the case or HBc) or contains several different viral proteins associated with nucleic acids, is not relevant with regard to the principle of the method. The viral envelope protein component, e.g. the HBs, acts as the linker between the reconstituted virosomal membrane and the nucleocapsid particle (e.g. the HBc), which, by itself, does not interact or associate with membrane structures efficiently. Although fundamentally different, the in vitro formulation process must to some extent mimic the conditions inside an HBV-infected cell to allow efficient interaction between HBs and HBc. In the present in vitro method, the assembly occurs during removal of the detergent, in the absence of any macromolecular cellular structures. In contrast, during HBV replication the HBs molecules are anchored in cellular membranes while interacting with the HBV nucleocapsid. Surprisingly and despite of the fundamentally different conditions, virus assembly—the packaging of a nucleocapsid particle into the viral envelope—occurs at high efficiency in our formulation procedure. Two processes have to occur simultaneously in order to link both antigens to the virosomal structure:
(i) the transmembrane proteins, influenza envelope (HA and NA) and HBs (the HBV envelope) have to integrate into the virosomal membrane, and
(ii) the HBc particles have to associate efficiently with HBs anchored in the membrane.

Accordingly, efficient HB-virosome assembly can only occur under optimised biochemical conditions and the correct stoechiometry of the individual components. The same holds true for the assembly virosomes comprising proteins from virus other than influenza-Virus and HBV. The integrity of the complex nucleocapsid structure is regarded as a prerequisite for its interaction with the membrane-anchored envelope protein.

In the present example, three distinct biological particle structures from independent sources are transformed in vitro into one novel type of synthetic virus-like particle, which is clearly distinct from any of the starting structures, and which does not exist in nature.

It is preferred, that the lipid recited in the above embodiment of the method of the invention comprises at least one phospholipid. More preferably, said phospholipids comprise phosphatidylcholine, phosphatidyletanolamine and phosphatidylserine.

It is also preferred in the method of the invention that said envelope proteins are the envelope proteins of a first and a second enveloped virus and the nucleocapsid particles are the nucleocapsid particles of said second enveloped virus.

In a further preferred embodiment of the method said first enveloped virus is influenza virus. More preferably, said envelope proteins are hemagglutinin (HA) and/or neuraminidase (NA).

It is further preferred in the method of the invention that said second enveloped virus is hepatitis B virus (HBV). More preferably, the nucleocapsid particle comprises HBc protein. Also preferably, the envelope protein is HBs protein.

According to the method of the invention it is preferred that prior to the step of solubilizing in step (a) a dilution of envelope proteins is centrifuged and the obtained pellet is solubilized in the detergent or lecithin solution in the presence of the lipid. Lipids which may be used in the method of the invention have been defined in more detail herein above.

It is further preferred that step (a) further comprises a sonication of the dilution prior to the centrifugation.

More preferably the centrifugation is performed for at least 2 h at 100,000 g and 4° C. and/or the sonication is performed for at least 2 min in a water bath at 37° C.

In one alternative of the method of the invention, said method may further comprise the step (b') performed subsequent of the step (b):
(b') sterile filtration of the dilution obtained in step (b).

Means and methods for the sterile filtration of a solution are known in the art. The sterile filtration e.g. may comprise the filtration of the dilution obtained in step (b) through a 0.22 μm filter as described in the appended examples.

The removal of the detergent in step (d) of the above described method of the invention may be achieved by:
(i) addition of Bio-Beads SM-2 and incubation of the dilution under rotation; and
(ii) removal of the Bio-Beads SM-2 from the dilution.

It is preferred that said steps (i) and (ii) are repeated with fresh Bio-Beads SM-2 for at least one time, preferably for at least two times.

It is also preferred, that steps (i) and (ii) are performed at room temperature.

Furthermore, also preferably, the incubation in step (i) is at least for 30 min.

It is also envisaged, that the method of the invention may comprise the step (e):
(e) sterile filtration of the dilution obtained in step (d).

Preferably, the detergent recited herein above is a non-ionic detergent. Examples for non-ionic detergents according to the invention comprise detergents e.g. such as octaethylene glycol mono(N-dodecyl)ether (OEG), Triton X-100, Triton X-114, NP 40, Tween 20/80 and lecithin. The detergents may be preferably used in a concentration range of 0.1 to 15% (v/v). Due to the nature of the detergents the preferred concentrations are generally given in (v/v). However, OEG is obtained in powder form and therefore, its concentration is preferably given in mM units. For example the concentration of 100 mM OEG corresponds to roughly 5.5% (v/v) OEG.

It is particularly preferred, that the non-ionic detergent is octaethylene glycol mono(N-dodecyl)ether (OEG).

It is also preferred for the method of the invention that OEG is adapted in step (b) to a concentration of in a rage of 20 mM to 100 mM. Most preferably said concentration is 50 mM (corresponding to about 2.75% OEG (v/v).

In a preferred embodiment of the method of the invention the adapted lipid:protein ratio is in the range between 1:10 and 20:1. More preferably said lipid:protein ratio is about 5:1.

It is preferred in the method of the invention that the portion of phosphatidylcholine in the virosome is 22%.

It is also preferred in the method of the invention that the ration of HA:viral envelope protein:viral capside protein is 1:1:1.

Moreover, it is preferred that the method of the invention comprises the addition of an adjuvant prior to the production of the virosomes in step (d).

A further alternative embodiment of the invention relates to the use of a virosome of the invention or a virosome produced by a method of the invention, for the preparation of a vaccine.

A further alternative embodiment of the invention concerns the use of a virosome of the invention or a virosome produced by a method of the invention, for the preparation of a vaccine for the prevention, alleviation or treatment of a HBV infection.

The invention also relates to a method for the vaccination of a subject comprising the step of administering a virosome of the invention or a virosome produced by a method of the invention to a subject in the need thereof. The virosome may be administered as described in general for pharmaceutical compositions herein above.

A further embodiment of the invention concerns a method for the vaccination of a subject for the prevention, alleviation or treatment of a HBV infection comprising the step of administering a virosome of the invention or a virosome produced by a method of the invention to a subject in the need thereof. Optionally the virosome may be administered in combination with a pharmaceutically acceptable carrier or diluent and/or an adjuvant.

It is particularly preferred that the above recited subjects are human.

TABLE 1

List of enveloped virus

| Virus family | Examples for human pathogens |
| --- | --- |
| Arenaviridae | Lymphocytic choriomeningitis virus (LCMV) |
| Bunyaviridae | Hantaan virus |
| Coronaviridae | SARS virus |
| Filoviridae | Ebola virus |
| Flaviviridae | Hepatitis C virus (HCV), Yellow Fever virus, Dengue virus, Tick-borne encelphalitis virus, West Nile virus |
| Hepadnaviridae | Hepatitis B virus (HBV) |
| Herpesviridae | Human herpes virus 1-5 |
| Orthomyxoviridae | Influenza A, B, C |
| Paramyxovirida | Respiratory syncytial virus (RSV), human parainfluenza virus (hPIV) |
| Poxviridae | Smallpox virus |
| Retroviridae | Human immunodeficiency virus (HIV) |
| Rhabdoviridae | Rabies virus |
| Togaviridae | Rubella virus | source: http://www.virology.net/Big_Virology/BVHostList.html

The figures show:

FIG. 1 Schematic drawings depicting the structure of the individual components and of the resulting HB-virosome are shown in FIG. 1. The analytical data are consistent with this proposed structure.

Figure 2:
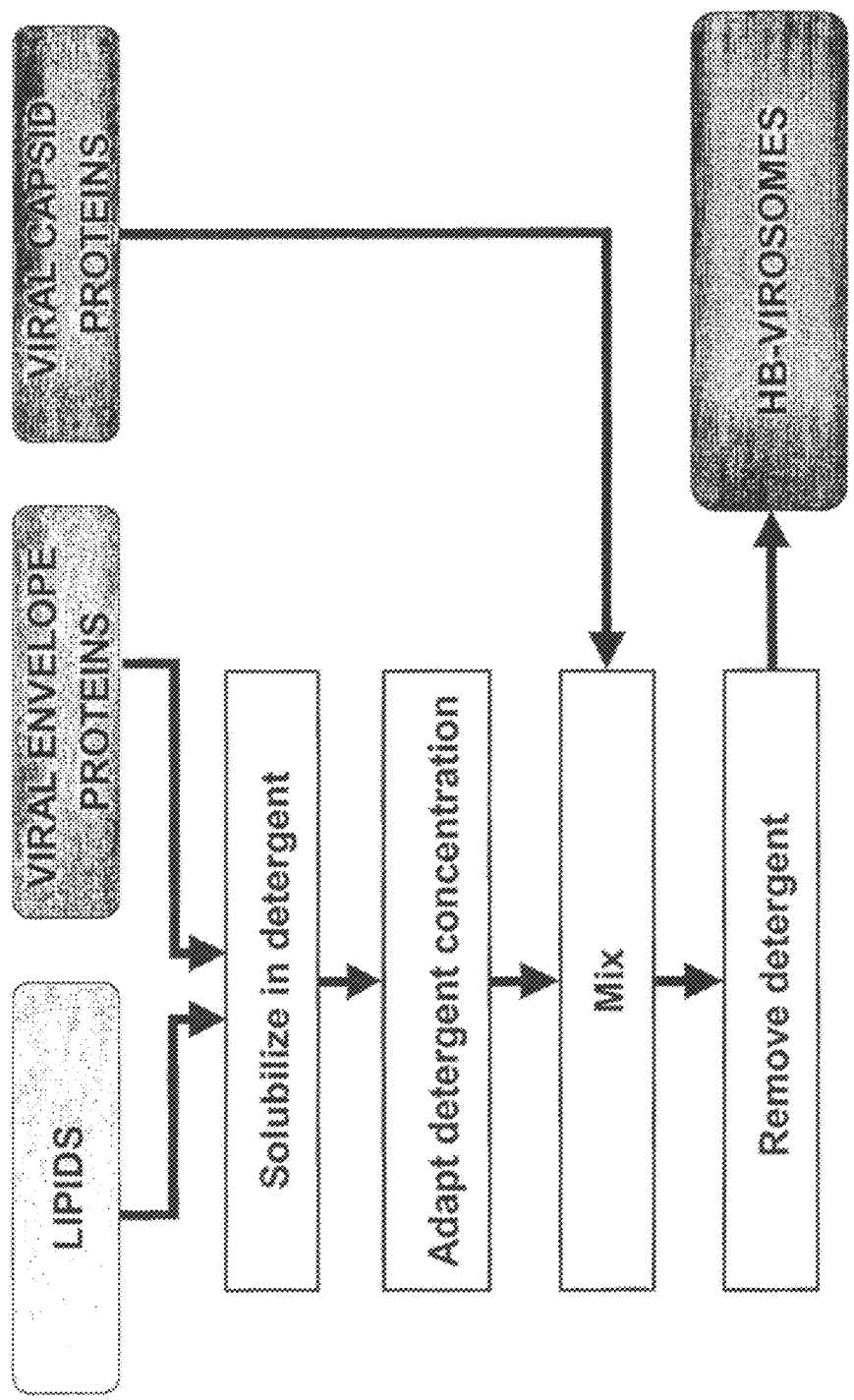

FIG. 2 Flow chart of the formulation process is shown in FIG. 2. The detailed formulation protocol for HB-virosomes is provided in the appended example.

Figure 3:
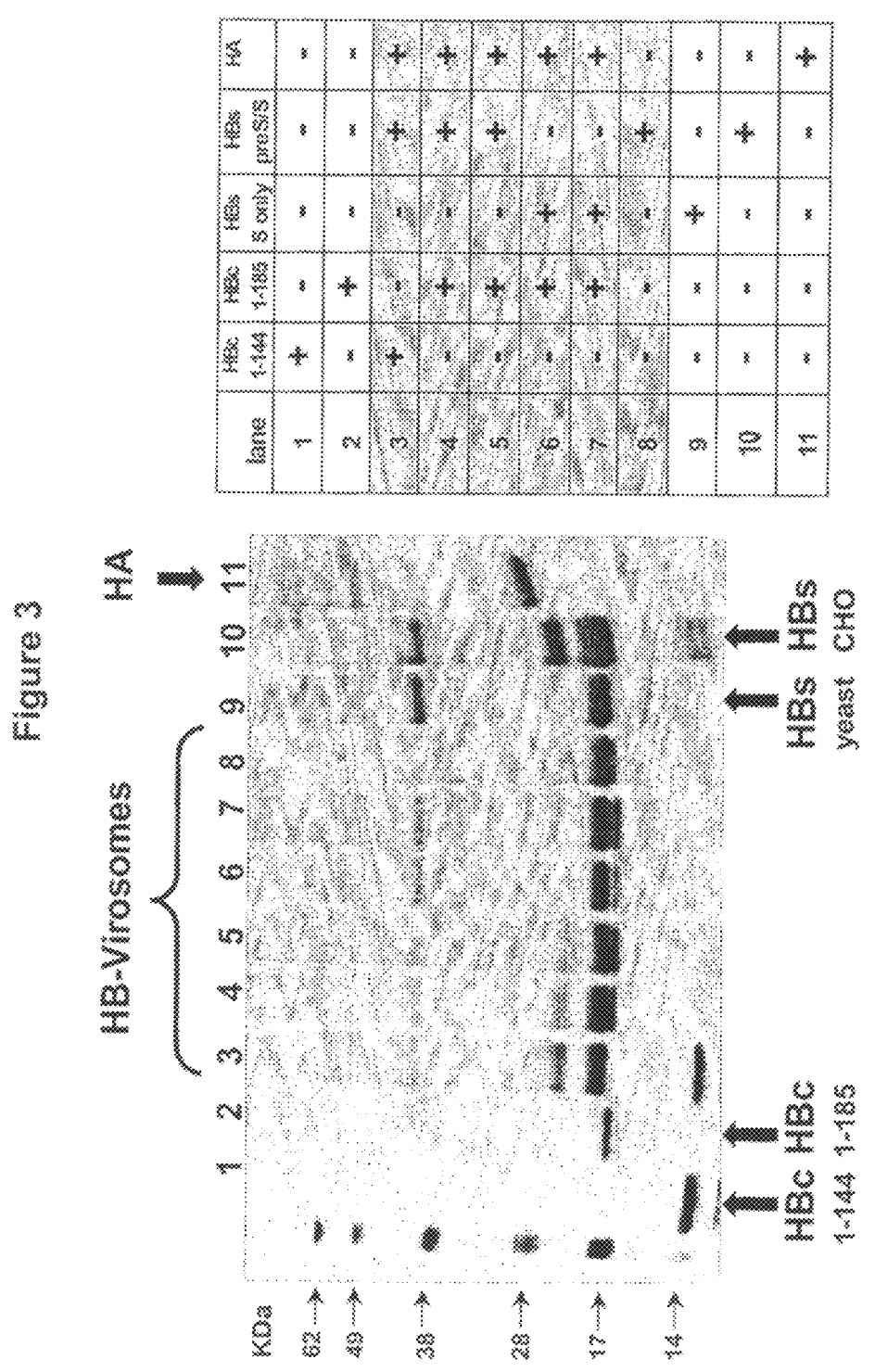

FIG. 3 shows the results of a SDS-PAGE analysis of HB-virosomes. The protein composition of HB-virosomes and of the starting materials (influenza, HBs, and HBc) is shown in FIG. 3 on a SDS-PAGE analysis.

The predicted physical structure of the HB-virosomas was confirmed by the following analytical results (FIG. 4-7)

Figure 5:
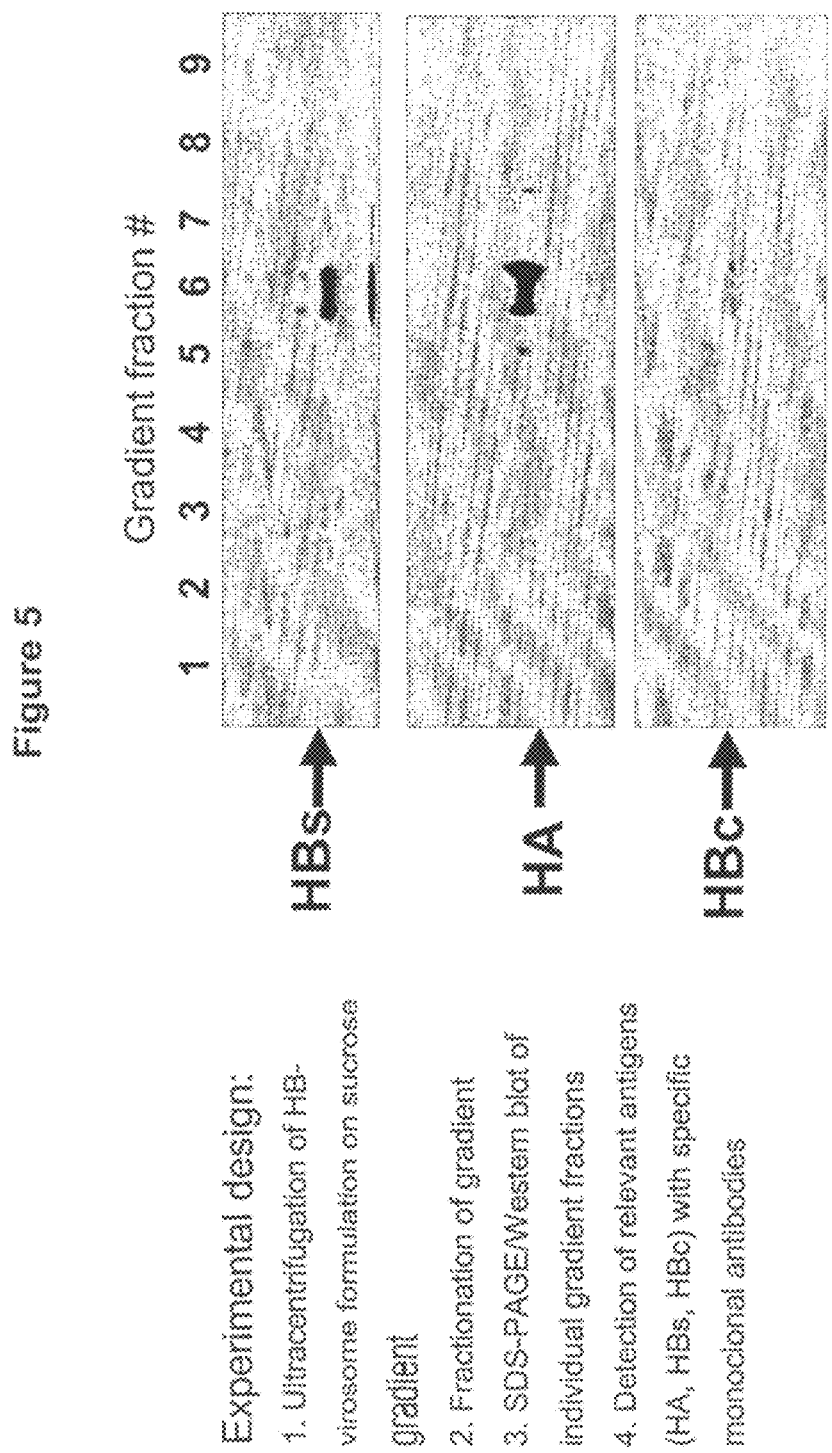

FIG. 4 shows the results of size analysis of HB-virosomes in comparison to the size of its individual components. HB-virosomes consists of one single type of particles distinct from individual components, represented as a single narrow peak in particle size distribution in Photon correlation spectroscopy FIG. 5 shows the results of a gradient fraction analysis of HB-virosomes. All antigens are found in the same gradient fraction after ultracentrifugation of HB-virosomes on a sucrose gradient, indicating their physical association.

Figure 6:
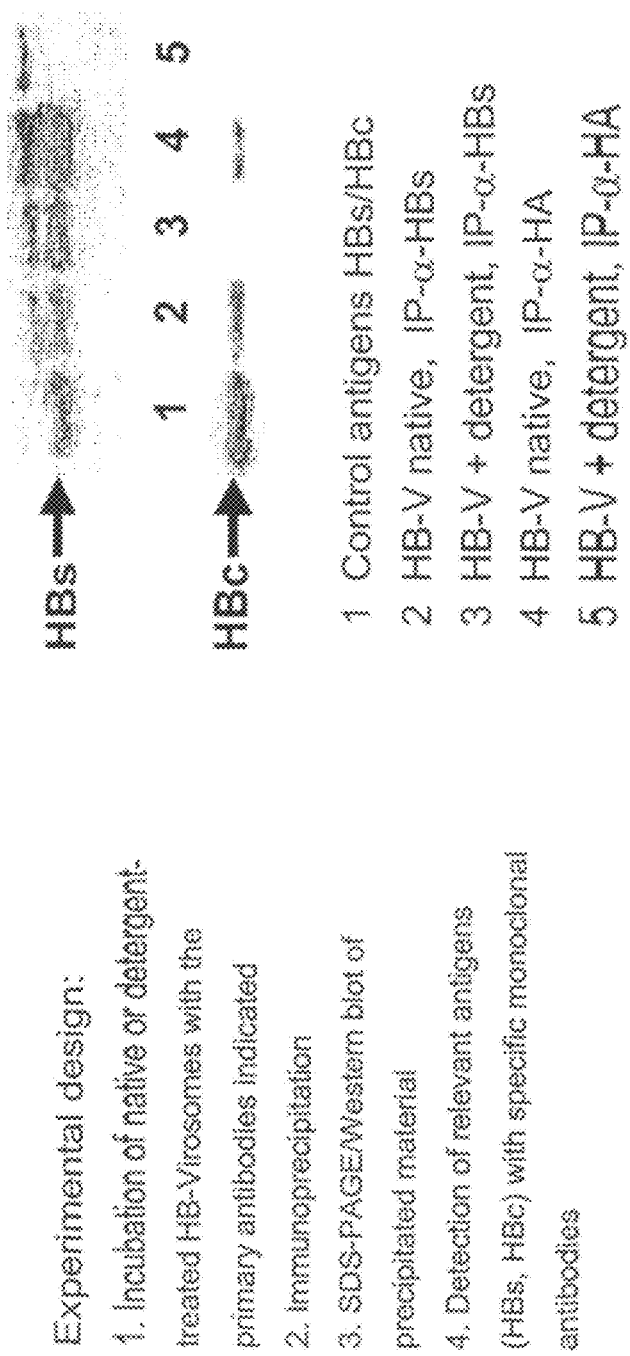
Figure 7:
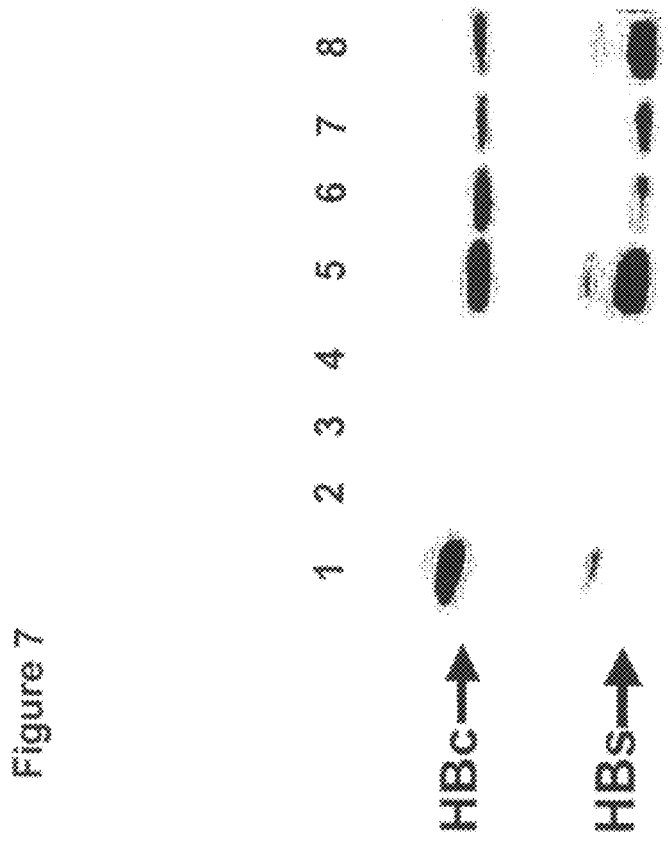
Figure 8:
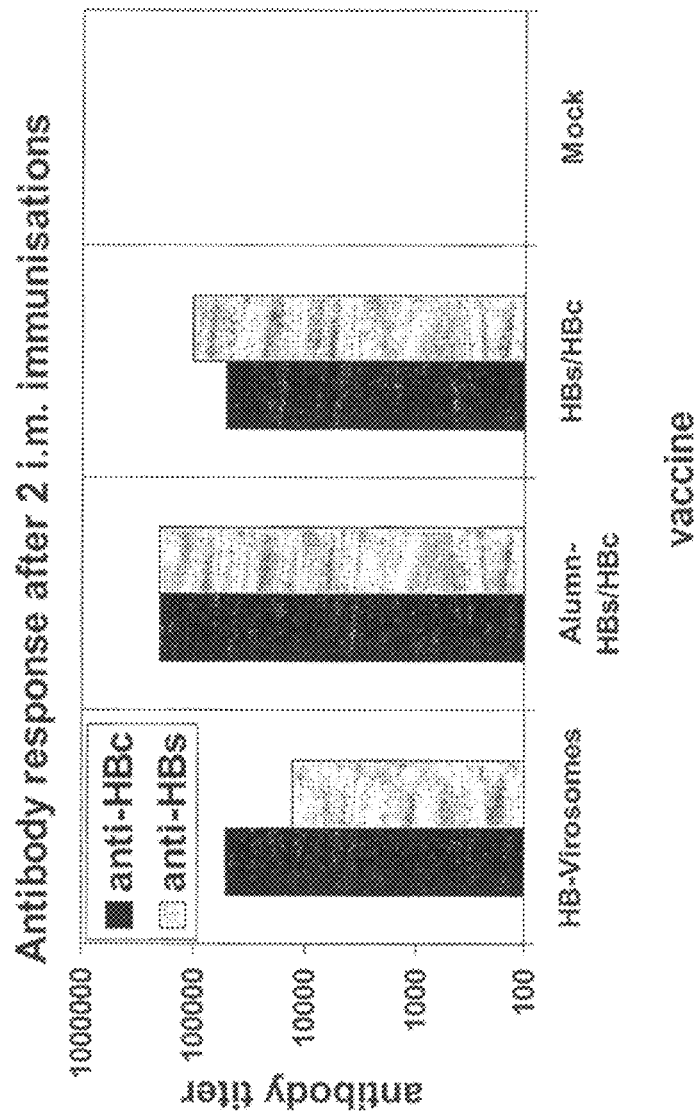
Figure 9:
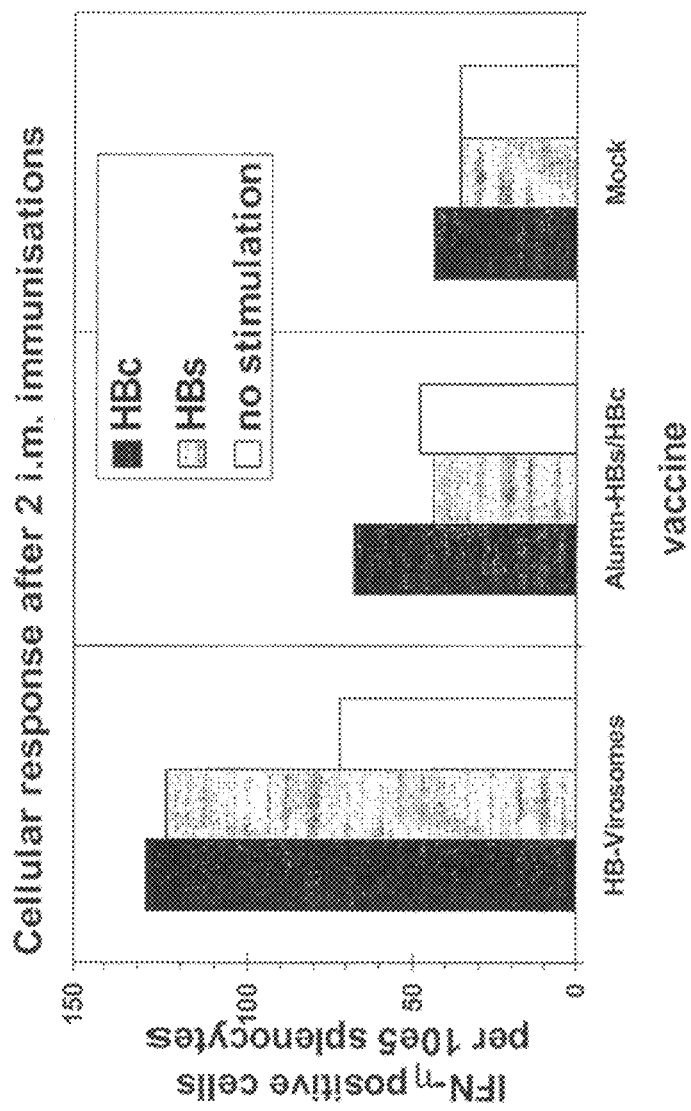

FIG. 6 shows the results of a SDS-PAGE/Western blot analysis of HB-virosomes. Immunoprecipitation of HB-virosomes using either anti-HA or anti-HBs antibody results in both cases in co-precipitation of all antigens (HBs, HBc and HA). If the HB-virosome structure is destroyed before immunoprecipitation by addition of detergent, only the antigen recognised directly by the antibody is precipitated (HA or HBs, respectively). This finding confirms that all antigens are associated in a single structure FIG. 7 shows the results of a SDS-PAGE Western blat analysis of HB-virosomes. When HB-virosomes are subjected to trypsin digest, both HBV antigens are partially protected (50%, according to Western blot). If the virosome structure is destroyed by addition of detergent before the incubation in trypsin, the HBV antigens are completely degraded within a short time FIG. 8 shows the results of a test of the antibody immune response to HB-virosomes after immunization of mice. Only preliminary data is available at this point on the immunogenicity of HB-virosomes. Experiments were performed in mice using HB-virosomes without an additional adjuvant. Mice were immunised via intramuscular injection with different amounts of HB-virosomes and high antibody titres against all three antigens were detected FIG. 9 shows the results of a test of the cellular immune response to HB-virosomes after immunization of mice. After a third boost, spleen cells were purified from immunised animals and, after re-stimulation in vitro with the respective antigens, the cellular response was determined by ELISPOT for Interferon-gamma. It has to be noted that this method does not differentiate between CD4 and CD8-type response.

FIG. 10 The summary table shows the immunological data obtained so far after immunisation with HB-virosomes. A humoral and a cellular response against both HBs and HBc were detectable in immunised animals.

The invention is now described by reference to the following examples which are merely illustrative and are not to be construed as a limitation of scope of the present invention.

EXAMPLE 1

Expression and Purification of HBsAg in Yeast

Schaefer S. et al., in *Hansenula polymorpha*: Biology and Applications, WILEY-VCH Verlag, Weinheim, 2002, Recombinant hepatitis B vaccines-disease characterization and vaccine production (p 187-p 193)

The process comprises the following steps: expression cassette and vector construction; transformation of yeast *Hansenula polymorpha*, strain selection and characterization, fermentation, cell harvest, cell disruption, clarification, adsorption, Ion exchange chromatography, ultrafiltration, ultracentrifugation, gel filtration chromatography, sterile filtration of final aqueous bulk.

Quality of final bulk material is specified by various biochemical assays such as Lowry, SDS/PAGE, Western Blot analysis, or AUSZYME.

EXAMPLE 2

Expression of HBc in E. Coli

Zheng et al, Journal of Biological Chemistry 1992, 13: 9422-9429

The structure of Hepadnaviral core antigens

Preikschat et al., Journal of General Virology 1999, 80: 1777-1788

Expression, assembly competence and antigenic properties of hepatitis B virus core gene deletion variants from infected liver cells.

The process comprises the following steps: expression cassette and vector construction; transformation of bacteria *Escherichia coli*, strain selection and characterization, fermentation, cell harvest, cell disruption, clarification, adsorption, chromatography, gel filtration, sterile filtration of final aqueous bulk.

Quality of final bulk material is specified by various biochemical assays such as Lowry, SDS/PAGE, Western Blot analysis.

EXAMPLE 3

Reconstitution of Influenza Virosomes

Glück R, 1995, Journal of Liposome Research 1995, 5(3), 467-479:

Liposomal Hepatitis A Vaccine and Liposomal multiantigen combination vaccines Influenza virosomes are produced from phospholipids and from Influenza virus, either grown in embryonated chicken eggs or in cell culture. The virus is harvested, purified and concentrated by one or more centrifugation steps, and subsequently inactivated by treatment with beta-propiolactone (BPL).

The inactivated virus is pelleted by ultracentrifugation and resuspended in a detergent (PBS containing 100 mM OEG) thereby dissolving the cuter shell of the virus, the viral envelope membrane whereas the inner part of the virus, the nucleocapsid remains a complex of proteins and residual nucleic acids. In parallel, the lipids (Lecithin and others) are dissolved in the same detergent (PBS containing 100 mM OEG). Lipids and dissolved influenza virus are then mixed and, optionally, treated with ultrasound pulses to complete the dissociation. Subsequently, a second ultracentrifugation step is performed in order to pellet and remove all insoluble material in the mixture. This insoluble material predominately includes the viral nucleocapsid complexes. The supernatant after ultracentrifugation contains all components of the future virosomes in solution: the viral envelope proteins and lipids and the phospholipids added separately. In a last step, the detergent is removed from the supernatant by batch-chromatography using SM-2 Bio-Beads. This sequential elimination of the detergent leads to the spontaneous formation of a homogeneous population of virosomal vesicles with a mean diameter of 100 to 200 nm, depending on the exact composition and the lipid:protein ratio.

EXAMPLE 4

Formulation and Analytics of HB-Virosomes

In order to achieve quantitative integration of the HBs and HBc components into HB-virosomes, the formulation process established for influenza-virosomes was modified significantly and optimised with respect to a number of variables. Using the standard influenza virosome protocol, the incorporation rate of the HBV antigens as well as the reproducibility of the process proved to be unsatisfactory.

4.1 Detailed Basic Formulation Protocol for HB-virosomes as Shown in FIGS. 3-11.

Inactivated influenza virus (strain A/Singapore) containing 2 mg HA and 2 mg of purified recombinant HBs antigen, both in phosphate buffered saline (PBS) were mixed and centrifuged for 2 hours at 100000 g, 4° C. The resulting pellet was solubilised in 1 ml of PBS containing 100 mM PBS-OEG.

Egg-derived phospholipids in powder form (16.5-mg phosphatidylcholine and 4.5 mg phosphatidyletanolamine) were dissolved in 1 ml 100 mM PBS-OEG.

Phospholipids and HA-HBs antigen solutions were then mixed and sonicated 2 minutes in a water bath at 37° to complete dissolution. Insoluble residual material was eliminated by centrifugation for 2 h at 100000 g, 4° C. The resulting supernatant (2 ml) was collected and diluted with PBS to a final volume of 3.5 ml.

The HBc antigen was diluted in PBS to 4 mg/ml and 0.5 ml of the dilution was added to the solution containing HA, HBs antigen and phospholipids in PBS-OEG, resulting in a final OEG concentration of 50 mM.

The formulation mix was filtrated through a 0.22-micrometer filter (Millipore) and subjected to the detergent removal procedure. The mixture was added to 1.2 g (dry weight) Bio-Beads SM-2 (BioRad) and incubated under rotation for 30 min at room temperature. Subsequently, the suspension was transferred to 0.8 g fresh Bio-Beads for 30 min incubation under the same conditions, followed by a third incubation with 0.8 g fresh Bio-Beads under identical conditions. The resulting HB-virosomes were then sterile filtered (0.22 micrometer) and stored in glass ampoules at 4° C. until use.

4.2 Possible Modifications of the Composition of HB-Virosomes

HB-virosomes containing HBV antigens from different sources (CHO-derived HBs, yeast-derived HBs), sub-types (ayw and adw HBV core particles) or variants (full size and truncated HBV core) were prepared in a similar manner. The preparation of reconstituted HB-virosomes, described above, resulted from series of formulation performed to identify critical parameters for particle size and antigen incorporation rate, and allowed a good antigen incorporation in particles of homogeneous size compatible with a final sterile filtration. Formulations with different phospholipid compositions, (phosphatidyl-ethanolamine and phosphatidylcholine in different ratios) showed an inversely proportional relationship between particle size and phosphatidylethanolamine content. The effect of lipid to protein ratio (2.5, 5, 6, 7.5) on size and antigen incorporation has been investigated in a series of formulations. The relative amount of the different antigens was shown to influence incorporation, increasing concentration of HA in formulations (without HBc antigen), lead to an increase of HBs antigen incorporation, reaching 80% for a 1 to 1 ratio. The following parameters were tested and optimised systematically:

Lipid:Protein Ratio

The optimal lipid:protein ratio is 5:1 in our hands, but a range of 20:1 to 1:10 for maximal antigen incorporation is conceivable if phospholipids are used. The lipid:protein ratio may vary even more if other lipids (synthetic lipids, steroid-type lipids) or combinations of different lipids are used.

Phospholipid composition (PC, PE, other lipids)

HB-virosomes with PC only can be produced, and, in our hands, 22% PE is optimal with regard to size and homogeneity. Again, if other lipids are used, these ratios may vary considerably.

Ratio Between Antigens (HA:HBs:HBc)

A ratio of 1:1:1 proved optimal in our hand. However, with modified lipid compositions and lipid:protein ratios, the optimal amounts for maximal antigen incorporation are likely to vary. In addition, formulations without any HA also yielded the desired particle structure.

Detergent

The detergent of choice is OEG at a concentration of 50 mM. However a range between 20 to 100 mM, may be applicable when modifying compositions and ratios. Other detergents of non-ionic, ionic, or zwitterionic nature may be used instead of OEG for the formulation process.

Other Non-ionic Detergent Candidates:

| Detergent | concentration range |
| --- | --- |
| Triton X-100 | 0.1 to 15% (v/v) |
| Triton X-114 | 0.1 to 15% (v/v) |
| NP40 | 0.1 to 15% (v/v) |
| Tween 20/80 | 0.1 to 15% (v/v) |

4.3 Analytics of Virosomal Formulation

A thorough physico-chemical analysis of HB-virosomes represents a crucial element for the optimisation of the formulation process and quality control of the future product. Thus, significant efforts were dedicated to the development of assays to investigate the content and the structure of HB-virosomes. Since the adjuvant effect (MHC-1 presentation) depends directly on the physical structure of the HB-virosomes, particular emphasis was given to the demonstration of a single particle type, which physically associates the HBV components of the vaccine with the virosomal carrier.

Quantification of Components:
  Proteins (SDS-PAGE)
  HBs (ELISA, Western blot)
  HBc (ELISA, Western blot)
  HA (SRD)
  Phospholipids (Enzymatic assay)
Virosome Structure:
  Photon correlation spectroscopy
  Co-Immunoprecipitation
  Density gradient ultracentrifugation
  Trypsin digestion
  Electron microscopy (planned)

Determination of Total Protein Concentration

Protein concentrations were measured by UV light absorption at wavelengths of 260, 280, and 320 nm and calculated according to the following formula: $1.55 \times (A_{280} - A_{320}) - 0.76 \times (A_{260} - A_{320})$. Results were expressed as milligrams per millilitre.

HBs and HBc Antigen Quantification

The amounts of HBs and HBc antigens incorporated in HB-virosome were determined by quantitative Elisa assays. To yield maximum access to antigen, the antigen standard and HB-virosome samples were dissolved in PBS-OEG during the first dilution, while successive dilutions were performed in PBS. HBs assay was performed using a commercial HBs Elisa detection kit (DADE Behring), serial dilutions of purified HBs antigen tested in the same assay allowed for a quantitative determination of antigens in the HB-virosome samples. For the quantitative HBc WLISA, microtitre plates were coated with a monoclonal antibody (mAb) directed against HBc (clone 7E6, Biogenesis, dilution 1:1000) in Na2CO3, 50 mM, pH 9.6. The plates were then blocked with BSA 1%, sucrose 5%, 0.05% NaN3 in PBS at room temperature for at least 1 hour, and washed with PBS containing 0.05% (v/v) Tween 20 (washing buffer) Samples (0.1 ml) were loaded and incubated for 1 hour at room temperature. A second, biotinylated mAb directed against HBc (clone 4H5, Biogenesis) was diluted 1:1000 in PBS with 0.05% Tween 20 and BSA 0.1% (dilution buffer), was added (0.1 ml per well) and incubated for 1 hour at room temperature. After four washes, plates were incubated in presence of streptavidin (1:5000 in dilution buffer) for 1 h at room temperature. After four additional washes, TMB (0.075 ml per well) was incubated 30 min and colour reaction was stopped with $H_2SO_4$, 1 M (75 µl per well) and the optical density at 450 nm was measured.

HA Quantification

HA contents of HB-virosomes were determined using a standard radial diffusion (SRD) assay. This test is a validated assay for analysis virosomal vaccines and was performed by the Berna Biotech Ltd. QC department in accordance with the respective SOP for Epaxal®.

Gel Electrophoresis, Western Blot, Silver Staining

In order to demonstrate the presence of HA, HBs or HBc antigens in HB-virosomes, samples from the formulation, gradient fractions, protease digestions, or co-immunoprecipitations, were separated on a NuPage Bis-Tris SDS-Page pre-cast gal (Invitrogen) with MES buffer and then transferred to a nitrocellulose membrane following manufacturer's instructions. Membranes were blocked with 5% milk in PBST (1% Tween20 in PBS) and incubated 1 h at room temperature with a 1:1000 dilution of the antigen specific antibody. Membranes were washed and then incubated 1 h with a 1:10.000 dilution of peroxidase-conjugated anti-rabbit or anti-sheep immunoglobulin. Proteins were visualised with ECL Plus substrate reagent (Amersham Pharmacia, Piscataway, N.J.).

Silver staining of gels was performed according to supplier's instruction (Invitrogen)

Particle Sizing: Photon Correlation Spectroscopy.

The hydrodynamic diameter, the polydispersity index, and the statistical particle size distribution of starting materials and formulated HB-virosomes was determined by Photon Correlation Spectroscopy or dynamic light scattering. This method relies on the size-dependent speed of Brown's movements, which is measured as the variation of light scattering over time. A Malvern Zetasizer 1000HS (Malvern Ltd, Malvern, UK) was used for this purpose, including the software for the calculation of the parameters from the raw data, change of light intensity. The samples were diluted adequately in PBS for measurement and 1 ml of the dilution was analysed under standard conditions at 25° C.

Sucrose Gradient

An ultracentrifugation through a discontinuous sucrose gradient was applied as analytical method to assess antigen incorporation in HB-virosomes structure, based on the distinct densities of the individual components. Aliquots of HB-virosome formulations in PBS were applied on the top of a 20-60% (w/v) discontinuous sucrose gradient in PBS and centrifuged at 100,000 g for 24 h at 4° C. The collected fractions were subsequently analysed for density, protein amount and by western blot for the presence of the different antigens.

Trypsin Digestion

Antigen incorporation and eventual encapsulation in HB-virosome particles was investigated via limited trypsin digestion. The processed samples were subsequently analysed by western blot for proteolysis-resistant fragments or full size protected protein. HB-virosomes were diluted either in PBS buffer (intact particles=native condition); or in 0.5% Na-deoxycholate and 1% Triton X100 in PBS (virosome structure destroyed=denaturing conditions). Protease digestion was performed with trypsin 5% (w/w protein) for 0, 2, 5 and 10 h at room temperature. As a control for effective accessibility of individual components to trypsin digestion, a mixture of the different antigens at the same concentration was digested in the same conditions. The reaction was stopped by adding 4×SDS-PAGE sample buffer. After 10-min denaturation at 95° C. digestion products were subjected to SDS-PAGE electrophoresis and immunoblot analysis for HBs and HBc.

Co-Immunoprecipitation

Physical association of HA, HBs and HBc antigens in HB-virosome structure was demonstrated by separate (individual) immuno-precipitation for each antigen under native and denaturing conditions (as described for trypsin digestion), and successive identification of Co-immunoprecipitated antigens by western blot analysis, immunoprecipitation of HB-virosome formulations was performed in parallel assays in the presence of specific antibodies for HA, HBc or HBs. Immune complexes were subsequently incubated 4 h with protein G-Sepharose coated beads (Promega) and centrifuged. The resulting pellet was washed five times with PBS. The immuno-precipitated proteins were resuspended by boiling 10 min in sample buffer and analysed by SDS-PAGE and Western blot. The presence of each antigen was investigated by incubation with the respective specific antibodies.

Virosomal Formulation: Immunogenicity in Mouse Model

Only preliminary data is available at this point on the immunogenicity of HB-virosomes. Experiments were performed in mice using HB-virosomes with or without an additional adjuvant, RC529 (Corixa). Mice were immunised via intramuscular injection with different amounts of HB-virosomes and high antibody titres against all three antigens were detected (FIG. 8). After a third boost, spleen cells were purified from immunised animals and, after re-stimulation in vitro with the respective antigens, the cellular response was determined by ELISPOT for Interferon-gamma (FIG. 9). It has to be noted that this method does not differentiate between CD4 and CD8-type response. In addition splenocytes from immunised animals were analysed by FACS (FIG. 10). Fresh splenocytes were directly stained with HBc-specific pentamers in combination with anti-CD8 antibody. Alternatively, splenocytes were stimulated with CD8-specific peptides or whole protein and subsequently stained for intracellular interferon-gamma in combination with either anti CD4 or anti-CD8 antibodies.

EXAMPLE 5

Applications of the Formulation Principle to other Viral Systems

The interaction between different viral proteins is crucial for virion assembly and is a general principle found for all viruses. Enveloped virus particles depend on cellular membrane structures for their assembly. The nucleocapsid, a complex of nucleic acids and proteins, associates with membrane-bound viral proteins in order to form the mature virus structure. We have shown for hepatitis B virus that this process can be mimicked in vitro, and in the absence of a cellular membrane structure and using viral proteins from different recombinant sources. Although a recombinant source of the viral antigens is preferable with regard to quantity and purity, the viral proteins may also be derived from the original virus, as applied here for influenza HA. The flexibility of the vitro formulation allows the inclusion of multiple antigens from different sources. Multivalent formulations containing proteins from several viruses (as shown for HBV and influenza) may improve the physical stability, the immunological properties, or the spectrum of protection of vaccines based on this principle.

It is conceivable that the same principle can be applied to any other enveloped virus, if the conditions are adapted to the respective pathogen and the necessary components are available in sufficient amounts. A number of candidates are listed below to which the in vitro formulation principle could be applied and which also represent attractive and urgent vaccine targets. However, whether or not the immune response induced by such hypothetical virus-like particles will have protective or even therapeutic effect cannot be predicted.

5.1 Hepatitis C Virus

HCV as the causative agent of hepatitis C represents a global health problem. It is estimated that % of the world population is infected this virus. No vaccine is currently available against HCV, neither for prophylactic nor for therapeutic use. The assembly of virus-like particles in cellular systems has been demonstrated (Baumert et al, Journal of Virology 1998, 75: 3827-3838; Hepatitis C virus structural proteins assemble into viruslike particles in insect cells). As in HBV, core protein monomers associate to an icosahedral nucleocapsid that interacts with membrane-anchored envelope proteins (E1, E2).

5.2 Other Flaviviruses

Aside from HCV, a number of relevant human pathogens are included in the family of flaviridiae: (West Nile virus, Kunjin virus, Japanese encephalitis virus, dengue virus, yellow fever virus, and tick-borne encephalitis virus). The similarity with HCV (and HBV) at the structural level is high and, therefore, an in vitro re-assembly of virus-like particles seems possible.

5.3 HIV

HIV is the most prominent member of the family of Retroviridae, Again, no effective vaccines are available despite of an urgent medical need. Although these viruses form a more complex nucleocapsid, an in vitro formulation of a multi-antigen vaccine based on the same principle as HB-virosomes appears feasible.

The invention claimed is:

1. A virosome comprising:
    a virosomal membrane comprising at least one lipid, an envelope protein of influenza virus, and an envelope protein of hepatitis B virus (HBV); and
    nucleocapsid particles comprising HBc protein of HBV, wherein the nucleocapsid particles are attached to the envelope proteins of HBV through an interaction between the envelope proteins of HBV and the HBc proteins of HBV, wherein a first plurality of the nucleocapsid particles so attached are located on the inside of the virosome, wherein a second plurality of the nucleocapsid particles so attached are located on the outside of the virosome, wherein the nucleocapsid protein HBc lacks an exposed lipophilic domain, and wherein the virosome is able to induce a therapeutic Th1 response to HBV infection.

2. The virosome of claim 1, wherein said at least one lipid comprises at least one phospholipid.

3. The virosome of claim 2, wherein the at least one phospholipid comprises a phospholipid selected from the group consisting of phosphatidylcholine, phosphatidylethanolamine, and phosphatidylserine.

4. The virosome of claim 1, wherein the envelope protein of influenza virus is hemagglutinin (HA).

5. The virosome of claim 1, wherein the envelope protein of HBV is HBs protein.

6. A vaccine comprising the virosome of claim 1, and a pharmaceutically acceptable carrier or diluent and/or an adjuvant.

7. The vaccine of claim 6, wherein the adjuvant is RC529.

8. A method for vaccinating a subject for the prevention, alleviation or treatment of an HBV infection, the method comprising:
    administering the virosome of claim 1 to the subject.

9. The method according to claim 8, wherein the virosome is in combination with a pharmaceutically acceptable carrier or diluent and/or an adjuvant.

10. The virosome of claim 1, wherein the envelope protein of influenza virus is neuraminidase (NA).

11. The virosome of claim 1, wherein the virosomal membrane comprises a second envelope protein of influenza virus.

12. The virosome of claim 11, wherein the envelope protein of influenza virus and second envelope protein of influenza virus are hemagglutinin (HA) and neuraminidase (NA).

13. A virosome comprising:
    a virosomal membrane comprising at least one lipid, at least one envelope protein of influenza virus, and hepatitis B virus (HBV) envelope protein HBs;
    nucleocapsid particles comprising HBV nucleocapsid protein HBc attached to the HBs protein, such that the HBc protein is located on the inside of the virosome; and
    nucleocapsid particles comprising HBV nucleocapsid protein HBc attached to the HBs protein, such that the HBc protein is located on the outside of the virosome,
    wherein nucleocapsid protein HBc lacks an exposed lipophilic domain, and
    wherein the virosome is able to induce a therapeutic Th1 response to HBV infection in a subject to which the virosome has been administered.

14. The virosome of claim 13, wherein the HBV envelope protein HBs comprises a mammalian glycosylation pattern, and wherein the HBV nucleocapsid protein HBc is bacterially-produced.

15. The virosome of claim 13, wherein the lipid is phosphatidylcholine, and wherein the envelope protein of influenza virus is hemagglutinin (HA).

16. The virosome of claim 15, wherein the lipid:protein ratio in the virosome is about 5:1, wherein the portion of phosphatidylcholine in the virosome is 22% by weight, and wherein the ratio of HA:HBs:HBc is 1:1:1.

17. The virosome of claim 13, wherein the HBV nucleocapsid protein HBc is selected from the group consisting of serotype ayw HBc, serotype adw HBc, full-size HBc, and truncated HBc.

18. The virosome of claim 13, wherein the HBV envelope protein HBs is produced and glycosylated in a cell selected from the group consisting of CHO cells and yeast cells.

* * * * *